(12) United States Patent
Kapur et al.

(10) Patent No.: US 10,878,818 B2
(45) Date of Patent: Dec. 29, 2020

(54) METHODS AND APPARATUS FOR SILENT SPEECH INTERFACE

(71) Applicants: Massachusetts Institute of Technology, Cambridge, MA (US); Shreyas Kapur, Cambridge, MA (US)

(72) Inventors: Arnav Kapur, Cambridge, MA (US); Shreyas Kapur, Cambridge, MA (US); Patricia Maes, Cambridge, MA (US)

(*) Notice: Subject to any disclaimer, the term of this patent is extended or adjusted under 35 U.S.C. 154(b) by 0 days.

(21) Appl. No.: 16/121,865

(22) Filed: Sep. 5, 2018

(65) Prior Publication Data

US 2019/0074012 A1   Mar. 7, 2019

Related U.S. Application Data

(60) Provisional application No. 62/554,509, filed on Sep. 5, 2017.

(51) Int. Cl.
*G10L 15/25*  (2013.01)
*G10L 15/24*  (2013.01)
(Continued)

(52) U.S. Cl.
CPC .......... *G10L 15/25* (2013.01); *A61B 5/04001* (2013.01); *A61B 5/0492* (2013.01);
(Continued)

(58) Field of Classification Search
CPC ... G10L 15/25; G10L 15/24; G10L 2015/225; G10L 15/16; H04R 1/14; H04R 1/46;
(Continued)

(56) References Cited

U.S. PATENT DOCUMENTS

| 8,200,486 B1 | 6/2012 | Jorgensen et al. |
| 8,836,638 B2 | 9/2014 | Madhvanath |

(Continued)

OTHER PUBLICATIONS

Chan, A., et al., Myo-electric signals to augment speech recognition; published in Medical and Biological Engineering and Computing, vol. 39, Issue 4, pp. 500-504, Jul. 2001.

(Continued)

*Primary Examiner* — Thierry L Pham
(74) *Attorney, Agent, or Firm* — Stephen R. Otis

(57) ABSTRACT

A system may detect silent, internal articulation of words by a human user, by measuring low-voltage electrical signals at electrodes positioned on a user's skin. The measured signals may have been generated by neural activation of speech articulator muscles during the internal articulation. The system may detect the content of internally articulated words even though the internal articulation may be silent, may occur even when the user is not exhaling, and may occur without muscle movement that is detectable by another person. The system may react in real-time to this detected content. In some cases, the system reacts by providing audio feedback to the user via an earphone or a bone conduction transducer. In other cases, the system reacts by controlling another device, such as a luminaire or television. In other cases, the system reacts by sending a message to a device associated with another person.

20 Claims, 6 Drawing Sheets

(51) Int. Cl.
  *A61B 5/00* (2006.01)
  *H04R 1/46* (2006.01)
  *A61B 5/04* (2006.01)
  *A61B 5/0488* (2006.01)
  *H04R 1/14* (2006.01)
  *A61B 5/0492* (2006.01)
  *G10L 15/16* (2006.01)
  *G10L 15/22* (2006.01)

(52) U.S. Cl.
  CPC ........ *A61B 5/04886* (2013.01); *A61B 5/4803* (2013.01); *A61B 5/682* (2013.01); *A61B 5/6814* (2013.01); *G10L 15/24* (2013.01); *H04R 1/14* (2013.01); *H04R 1/46* (2013.01); *A61B 2562/04* (2013.01); *G10L 15/16* (2013.01); *G10L 2015/225* (2013.01); *H04R 2201/107* (2013.01); *H04R 2460/13* (2013.01)

(58) Field of Classification Search
  CPC .......... H04R 2460/13; H04R 2201/107; A61B 5/682
  USPC ........................................................ 704/231
  See application file for complete search history.

(56) References Cited

U.S. PATENT DOCUMENTS

| | | | | |
|---|---|---|---|---|
| 2003/0144601 | A1* | 7/2003 | Prichep | A61B 5/7203 600/544 |
| 2005/0101875 | A1* | 5/2005 | Semler | A61B 5/04085 600/509 |
| 2008/0103769 | A1 | 5/2008 | Schultz et al. | |
| 2009/0214060 | A1* | 8/2009 | Chuang | A61B 5/6814 381/151 |
| 2010/0185115 | A1 | 7/2010 | Causevic et al. | |
| 2015/0338917 | A1* | 11/2015 | Steiner | H04L 9/3231 345/156 |
| 2016/0314781 | A1* | 10/2016 | Schultz | A61B 5/04886 |
| 2017/0249009 | A1 | 8/2017 | Parshionikar | |

OTHER PUBLICATIONS

Denby, B., et al., Silent speech interfaces; published in Speech Communication, vol. 52, Issue 4, pp. 270-287, Apr. 2010.

Hueber, T., et al., Acquisition of ultrasound, video and acoustic speech data for a silent-speech interface application; 8th International Seminar on Speech Production (2008).

Jorgensen, C., et al., Subauditory Speech Recognition based on EMG/EPG Signals (2003).

Jorgensen, C., et al., Web Browser Control Using EMG Based Sub Vocal Speech Recognition; published in Proceedings of the 38th Annual Hawaii International Conference on System Sciences, IEEE 2005.

Jou, S., et al., Towards continuous speech recognition using surface electromyography; published in Proceedings Interspeech 2006.

Jou, S., et al., Continuous Electromyographic Speech Recognition with a Multi-Stream Decoding Architecture; published in 2007 IEEE International Conference on Acoustics, Speech and Signal Processing ICASSP '07.

Maier-Hein, L., et al., Session independent non-audible speech recognition using surface electromyography; published in IEEE Workshop on Automatic Speech Recognition and Understanding, 2005.

Phinyomark, A., et al., Feature Reduction and Selection for EMG Signal Classification; published in Expert System with Applications, vol. 39, Issue 8, pp. 7420-7431, Jun. 2012.

Wand, M., et al., Session-independent EMG-based Speech Recognition; published in Biosignals, 2011.

* cited by examiner

METHODS AND APPARATUS FOR SILENT SPEECH INTERFACE

RELATED APPLICATIONS

This application claims the benefit of U.S. Provisional Application No. 62/554,509 filed Sep. 5, 2017 (the "Provisional").

FIELD OF TECHNOLOGY

The present invention relates generally to silent speech interfaces.

COMPUTER PROGRAM LISTING

The following seven computer program files are incorporated by reference herein: (1) 1DCNN_fft_keras.txt with a size of about 3 KB; (2) 1DCNN_keras_from_arnav.txt with a size of about 5 KB; (3) digits_keras_no_shuffle_feature-_selection.txt with a size of about 19 KB; (4) model_repo.txt with a size of about 46 KB; (5) realtime_processing.txt with a size of about 13 KB; (6) utils.txt with a size of about 41 KB; and (7) vad_fused_keras_no_shuffle.txt with a size of about 22 KB. Each of these seven files were created as an ASCII .txt file on Aug. 24, 2018.

BACKGROUND

Ordinary speech includes at least three components: (a) respiration; (b) phonation; and (c) articulation.

During ordinary speech, respiration involves exhaling slowly while making sounds (e.g., words).

During ordinary speech, phonation occurs in the vocal cords and larynx, while the vocal cords vibrate.

During ordinary speech, articulation involves "shaping" sound into phonemes. During ordinary speech, articulation may occur when two speech organs move close together, such as two lips coming together, or a tongue tip touching upper teeth.

SUMMARY

In illustrative implementations of this invention, a silent speech interface (SSI) system detects silent, internal articulation of words by a human user. The SSI system may do so by measuring low-voltage electrical signals at electrodes positioned on a user's skin, on the user's face or neck. The measured signals may have been generated by neural activation of speech articulator muscles during the internal articulation. The system may detect the content of internally articulated words even though the internal articulation: (a) may be silent; (b) may occur even when the user is not exhaling; and (c) may occur without muscle movement that is detectable by another person. The system may react in real-time to this detected content. In some cases, the system reacts by providing audio feedback to the user via an earphone or a bone conduction transducer. In other cases, the system reacts by controlling another device, such as a luminaire or television. In other cases, the system reacts by sending a message to a device associated with another person.

In illustrative implementations, the SSI system may detect the content of internal articulation by a first person, where the internal articulation is not detectable by the unaided senses of any other person.

During the internal articulation, respiration may be normal—that is, a user may internally articulate while inhaling, while holding the breath, or while exhaling. This is unlike ordinary speech (ordinary speech occurs while exhaling slowly).

The internal articulation may cause, trigger, or involve neural activation of one or more Articulator Muscles. This neural activation may be detected by the SSI system, and may occur simultaneously with the internal articulation. As used herein, "Articulator Muscles" means the following muscles: geniohyoid, mylohyoid, genioglossus, superior longitudinal, inferior longitudinal, transverse, vertical, hyoglossus, palatoglossus, styloglossus, levator palatini, musculus uvulae, tensor palatini, palatopharyngeus, superior pharyngeal constrictor, medial pharyngeal constrictor, and inferior pharyngeal constrictor.

In some cases, the internal articulation (which is detected by the SSI system) causes no movement of the Articulator Muscles. In some cases, internal articulation by a user (which is detected by the SSI system) causes only very slight movement of the Articulator Muscles, which movement is not detectable by the unaided senses of any other person. This very slight movement: (a) may be subjectively experienced by the user as little or no movement; and (b) may be associated with a subtle electrical signal (in efferent nerves or neuromuscular junctions) that is measured by the SSI system.

In some cases, a user's internal articulation of a word is subjectively perceived by the user as silently forming the word in the vocal tract, while not moving any muscle in the head or neck. In some cases, a user's internal articulation of a word is subjectively perceived by the user as silently forming the word in the vocal tract, while not moving any speech muscle. In some cases, a user's internal articulation of a word is subjectively perceived by the user as silently forming the word in the vocal tract, while not moving any speech articulator muscle. In some cases, a user's internal articulation of a word is subjectively perceived by the user as silently forming the word in the vocal tract, while making little or no movement of any muscle in the head or neck. In some cases, a user's internal articulation of a word is subjectively perceived by the user as silently forming the word in the vocal tract, while making little or no movement of any speech muscle. In some cases, a user's internal articulation of a word is subjectively perceived by the user as silently forming the word in the vocal tract, while making little or no movement of speech articulator muscle.

In some cases, a user's internal articulation of a word is subjectively perceived by the user as mentally forming the word, while being aware of—but not moving—speech muscles. In some cases, a user's internal articulation of a word is subjectively perceived by the user as mentally forming the word, while being aware of—but not moving—speech articulator muscles. In some cases, a user's internal articulation of a word is subjectively perceived by the user as mentally forming the word, while being aware of—but making little or no movement of—speech muscles. In some cases, a user's internal articulation of a word is subjectively perceived by the user as mentally forming the word, while being aware of—but making little or no movement of—speech articulator muscles.

In some cases, a user's internal articulation of a word is subjectively perceived by the user as an intent (a) to silently form the word in the vocal tract and (b) to not move any muscle in the head or neck. In some cases, a user's internal articulation of a word is subjectively perceived by the user as an intent (a) to silently form the word in the vocal tract and (b) to not move any speech muscle. In some cases, a user's internal articulation of a word is subjectively perceived by the user as an intent (a) to silently form the word in the vocal tract and (b) to not move any speech articulator muscle. In some cases, a user's internal articulation of a word is subjectively perceived by the user as an intent (a) to silently form the word in the vocal tract and (b) to make little or no movement of any muscle in the head or neck. In some cases, a user's internal articulation of a word is subjectively perceived by the user as an intent (a) to silently form the word in the vocal tract and (b) to make little or no movement of any speech muscle. In some cases, a user's internal articulation of a word is subjectively perceived by the user as an intent (a) to silently form the word in the vocal tract and (b) to make little or no movement of any speech articulator muscle.

In some cases, a user's internal articulation of a word is subjectively perceived by the user as intensely and silently reading the word, or as intensely thinking the word.

In illustrative implementations, the SSI system detects small voltage signals that are characteristic of internal articulation. These small voltage signals may comprise myoneural electrical signals that occur at neuromuscular junctions during internal articulation, or may comprise neural electrical signals that occur in efferent nerve fibers during internal articulation, or may comprise both.

These small voltage signals (which are characteristic of internal articulation): (a) may have much smaller voltages than voltages that occur during ordinary speech; (b) may have much smaller voltages than voltages that occur during gross movements of one or more facial muscles; and (c) may have much smaller voltages than voltages that occur during gross movements of the lips.

For instance, in some cases, a small voltage signal (produced during internal articulation by a user) may have a root mean square (RMS) voltage that is less than one half of the RMS voltage that would occur during exaggerated, mouthed, ordinary speech of the user. In some cases, a small voltage signal (produced during internal articulation by a user) may have a RMS voltage that is less than one half of the RMS voltage that would occur during mouthed, ordinary speech of the user. In some cases, a small voltage signal (produced during internal articulation by a user) may have a RMS voltage that is less than one half of the RMS voltage that would occur during audible speech by the user with visible lip movements. In some cases, a small voltage signal (produced during internal articulation by a user) may have a RMS voltage that is less than one half of the RMS voltage that would occur during audible speech by the user with lip movements that are visible and larger than mean size for the user. In some cases, a small voltage signal (produced during internal articulation by a user) may have a RMS voltage that is less than one half of the RMS voltage that would occur during ordinary speech by the users. In some cases, a small voltage signal (produced during internal articulation by a user) may have a RMS voltage that is less than one third of the RMS voltage that would occur during exaggerated, mouthed, ordinary speech of the user. In some cases, a small voltage signal (produced during internal articulation by a user) may have a RMS voltage that is less than one third of the RMS voltage that would occur during mouthed, ordinary speech of the user. In some cases, a small voltage signal (produced during internal articulation by a user) may have a RMS voltage that is less than one third of the RMS voltage that would occur during audible speech by the user with visible lip movements. In some cases, a small voltage signal (produced during internal articulation by a user) may have a RMS voltage that is less than one third of the RMS voltage that would occur during audible speech by the user with lip movements that are visible and larger than mean size for the user. In some cases, a small voltage signal (produced during internal articulation by a user) may have a RMS voltage that is less than one third of the RMS voltage that would occur during ordinary speech by the user.

In some cases, where a reference electrode is positioned on the rear side of an earlobe and where the measurement electrodes are placed in a configuration shown in either FIG. 5, 6, 7 or 8, a low voltage signal (produced during internal articulation) that is measured at the measurement electrodes may have an RMS voltage that is greater than or equal to 8 microvolts and less than or equal to 20 microvolts.

In illustrative implementations, the SSI system measures voltages over time at a set of surface electrodes. For instance, in some cases, the surface electrodes are positioned on the skin in any one or more of the following anatomical regions of the head or neck: mental (chin), oral (upper and lower lips), buccal (maxillary), submaxillary, submental, hyoid, carotid fossa, and infraorbital.

In illustrative implementations, the measured voltage at a given measurement electrode may be the difference between the electrical potential at the given electrode and the electrical potential at a reference electrode. For instance, in some cases, the reference electrode may be a surface electrode that is positioned on the rear of an earlobe or on the wrist.

In illustrative implementations, the SSI system may extract (or effectively extract), from a set of voltages measured by surface electrodes, a signal of interest that comprises a low voltage signal produced by internal articulation.

The SSI system may extract the signal of interest in different ways.

In some cases, a signal of interest (that comprises a low voltage signal produced by internal articulation) is extracted (from a set of electrode measurements) by excluding temporal frames in which the measured RMS voltage is greater than a cutoff voltage. For instance, in some cases: (a) voltage is measured at multiple surface electrodes over time; (b) a digital signal is outputted for each electrode, which signal encodes voltage measurements taken at that electrode at different times; (c) each signal is mean normalized, bandpass filtered (e.g., with a passband of 1 Hz to 10 Hz), and optionally notch filtered (e.g., with a narrow bandstop centered at 60 Hz); (d) for each temporal period (e.g., 4 seconds), the signals for the multiple electrodes for the temporal period are concatenated into a single 1D vector of measurements (a "measurement frame"); and (d) for each measurement frame, (i) RMS voltage is computed for the measurement frame; (ii) if the RMS voltage is greater than a cutoff voltage, the measurement frame is excluded and not further processed; and (iii) if the RMS voltage is less than or equal to the cutoff voltage, the measurement frame is retained and further processed. For example, in some cases, the cutoff voltage is 80 microvolts. However, the cutoff frequency may vary, depending on many factors, including hardware (e.g. type of electrodes), whether a conductive paste is employed, skin impedance, and electrode placement, including position of the reference electrode.

In some cases, a signal of interest (that comprises a low voltage signal produced by internal articulation) is extracted (from a set of electrode measurements) by excluding voltage spikes above a specified threshold. For instance, in some cases: (a) voltages are sampled at a 250 Hz sampling frequency; and (b) for each sample in a concatenated stream of measurements (i) the sample is excluded if the voltage of the sample exceeds a baseline by more than a specified threshold (e.g., by more than 30 microvolts) and (ii) the sample is retained for further processing if the voltage does not exceed the baseline by more than the specified threshold. For instance, the baseline for a given sample may be calculated as the average voltage in eight samples consisting of four samples immediately preceding (in time) the given sample and of four samples immediately following (in time) the given sample.

In some cases, "dead" periods in which voltages are very low or zero are excluded from the signal of interest. For instance, a convolutional neural network (CNN) may exclude "dead" measurement frames in which no signals from internal articulation are detected (such as measurement frames in which RMS voltage is very low or zero).

Alternatively, in some cases, a signal of interest (that comprises a low voltage signal produced by internal articulation) is extracted by a neural network (e.g., a CNN) without explicitly excluding voltages above a cutoff frequency and without explicitly excluding voltage spikes. Instead, in this alternative approach, the neural network (e.g., CNN) may be trained on a training set of voltage measurements taken during internal articulation, and may thereby machine learn to extract the signal of interest.

In illustrative implementations, the SSI system enables a human user to communicate silently with other humans or other devices, in such a way that the communication is not detectable by another human (other than an intended human recipient of the communication).

In some cases, the SSI system provides feedback that is audible to a human user wearing the SSI system, but that is not audible to other persons in the vicinity of that user. For instance, the SSI system may include a bone conduction transducer that is positioned either behind, or slightly in front of, an ear. Or, for example, the SSI system may include an earphone.

In some cases, the SSI system performs closed-loop feedback, where neither the silently articulated input (from a user wearing the SSI system) nor the feedback to the user is detectable by other persons in the vicinity of the user. Among other things: The SSI system may function as a "world clock". For instance, in some cases: (a) a user silently and internally articulates a request for the current time in a particular city; and (b) the SSI system detects the content of this request and outputs to the user (via a bone conduction transducer) the current time in that city. Likewise, the SSI system may perform math calculations for the user. For example, in some cases: (a) a user silently and internally articulates multiple numbers and a request for a mathematical operation; and (b) the SSI system detects the content of this request and outputs to the user (via a bone conduction transducer) the result of the mathematical operation on the numbers. Also, the SSI system may play a game with the user. For instance, in some cases: (a) a user silently and internally articulates a chess move (e.g., "Qg5", which means move the Queen to the g5 square of a chessboard); and (b) the SSI system detects the content of this chess move and simulates another player by outputting to the user (via a bone conduction transducer) a responding chess move (e.g., "Ngf3"). In each example in this paragraph, the feedback may be audible to a human user wearing the SSI system yet not audible to other persons in the vicinity of that user.

In some cases, the closed-loop feedback provides information to the user, where the information is obtained from the Internet or from another database external to the SSI system. For instance, in some cases: (a) a user silently and internally articulates a request for the weather; and (b) the SSI system detects the content of this request, obtains the weather from the Internet, and then outputs to the user (via a bone conduction transducer) the weather. Again, the feedback may be audible to the human user wearing the SSI system yet not audible to other persons in the vicinity of that user.

In some cases, the SSI system operates in open-loop mode. For example, the SSI system may be used to control IoT (internet of things) appliances, such as turning on or off a fan or a light, controlling a television, or controlling a HVAC (heating, ventilation and air conditioning) system. Likewise, the SSI system may be used to provide any input (e.g., input to make a reservation, or input to an Augmented Reality or Virtual Reality application). For instance, in some cases: (a) a user silently and internally articulates an input; and (b) the SSI system detects the content of this input and outputs an instruction to an external device, which instruction is in accordance with the input.

In some cases, the SSI system facilitates private human-to-human communication. For instance, the SSI system: (a) may detect the content of speech that is internally articulated by a first user wearing the SSI system; (b) may send a first message to another human (e.g., to a mobile device or computer associated with the other human), which first message comprises the detected content; (c) may receive a second message from the other human (e.g., from a mobile device or computer associated with the other human); and (d) may convert the second message into data representing sound and may output the second message to the first user. The second message may be audible to the first user (who is wearing the SSI system) yet not audible to other persons in the vicinity of the first user. In the preceding sentence, the entire two-way communication may be undetectable by other persons in the vicinity of the first user (who is internally articulating).

In illustrative implementations, this invention has many practical advantages. For instance, in illustrative implementations, the SSI system facilitates private communication by a user wearing the SSI, in such a way that neither the content of the communication, nor the fact that communication is occurring, is detectable by persons in the vicinity of the user. Likewise, in many cases, the SSI system is wearable and portable.

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the Field of Technology section is not limiting; instead it identifies, in a general, non-exclusive manner, a field of technology to which some implementations of this invention generally relate.

The above Figures are not necessarily drawn to scale. The above Figures show some illustrative implementations of this invention, or provide information that relates to those implementations. The examples shown in the above Figures do not limit this invention. This invention may be implemented in many other ways.

DETAILED DESCRIPTION

In illustrative implementations, an SSI system detects the content of internally articulated words even though: (a) the internal articulation may be completely silent (to the unaided hearing of another person); and (b) the internal articulation may occur without movement of any external muscles (that is detectable by the unaided vision of another person). For instance, internal articulation by a user may occur without movement of the user's lips or facial muscles.

Thus, the SSI system may detect the content of internal articulation by a first person, where the internal articulation is not detectable by the unaided senses of any other person.

Figure 1:
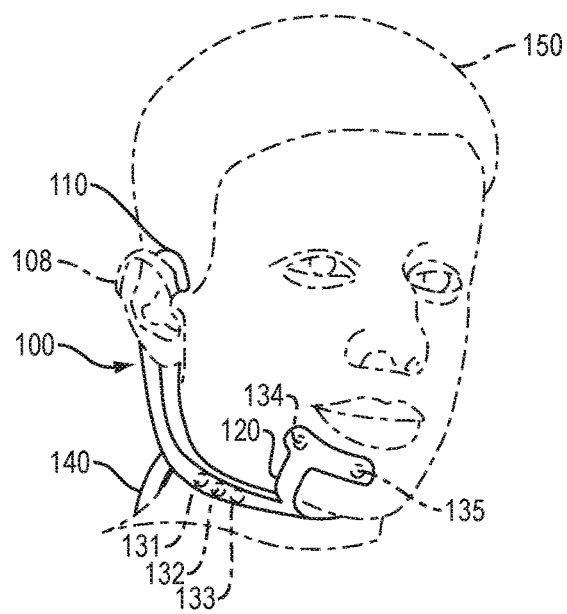
FIG. 1 shows a user wearing a silent speech interface.

FIG. 1 shows a user wearing a silent speech interface (SSI) device. In the example shown in FIG. 1, the SSI device 100 is configured to be worn adjacent to the head and neck of a user 150. SSI device 100 includes a curved structure 110. When the SSI device is being worn by the user, curved structure 110 may curve around and above, and may be supported by, the user's ear. SSI device 100 may house a bone conduction transducer 108 that is positioned behind the user's ear and that outputs vibrations that may be heard by the user but not by other persons in the user's environment. SSI device 100 may include a clip-on extension 120. Both extension 120 and the main body of SSI device 100 may house electrodes. In FIG. 1, a portion of the main body of SSI device 100 extends below the jawline and houses electrodes 131, 132, and 133 that are worn on the user's skin in the submaxillary region. Likewise, in FIG. 1, clip-on extension 120 houses electrodes 134 and 135 that are worn on the user's skin in the oral (lip) region and mental (chin) region, respectively. Sensors 134 and 135 are electrically connected to the main body of SSI device 100 via wired connection 144. SSI device 100 may be configured to communicate wirelessly (e.g., by wireless transmission in accordance with a Bluetooth® protocol) with one or more computers or other electronic devices. Alternatively or in addition, wired connection 140 may allow SSI device 100 to communicate with one or more other computers or electronic devices.

Figure 2:
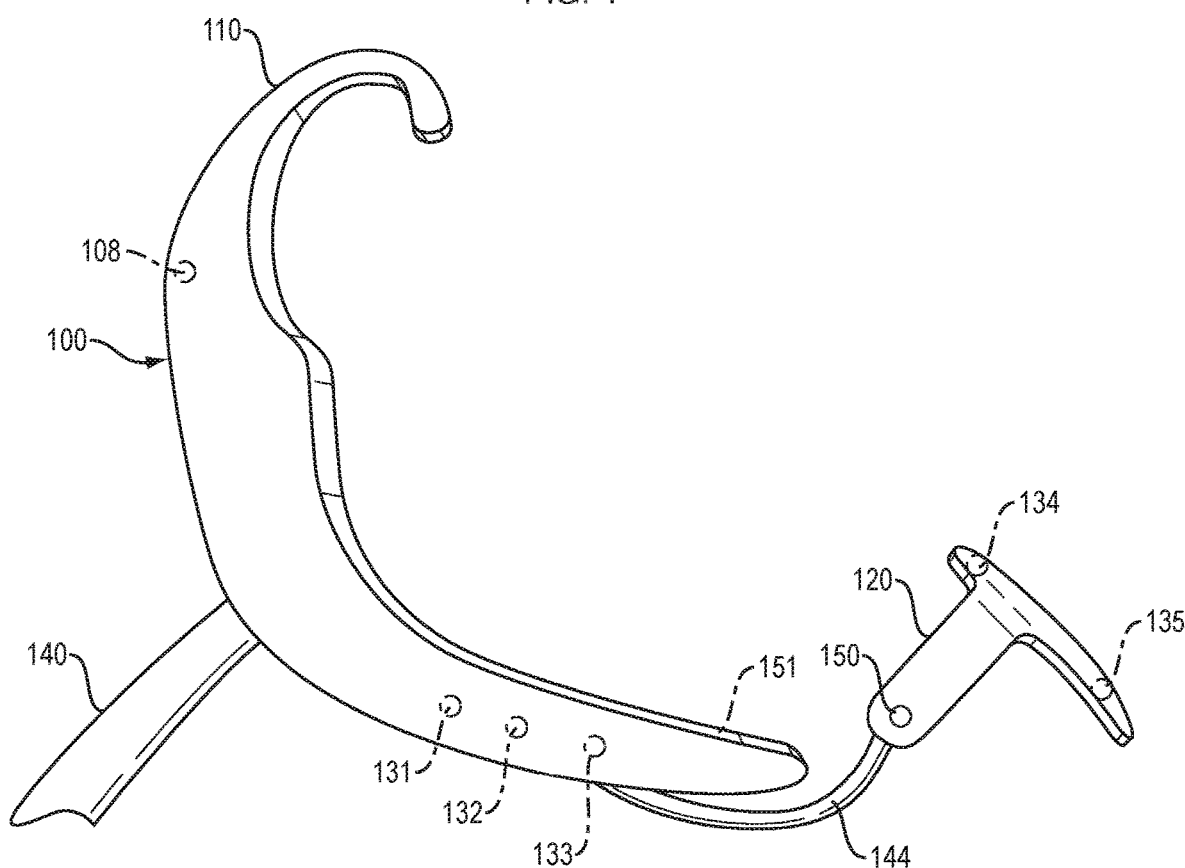
FIG. 2 shows a silent speech interface.

FIG. 2 shows a close-up view of the same SSI device 100 as that shown in FIG. 1. In the example shown in FIG. 2, clip-on extension 120 may be attached to the main body of SSI device 100 by clips 150, 151. These clips 150, 151 may be configured in such a way that clip-on extension 120 is easily attachable to, and detachable from, the main body of SSI device 100, without damage.

In the example shown in FIGS. 1 and 2, SSI device 100 is wearable, portable, and lightweight. Furthermore, SSI device 100 may be configured to be "always on", or almost always on, or frequently on. For example, SSI device 100 may have a battery and a slow rate of energy consumption that together allow the SSI device 100 to operate for hours or days before recharging the battery.

In FIGS. 1 and 2, SSI device 100 is sufficiently rigid so that the electrodes do not, during a particular use session, shift position relative to the portion of the user's skin which they are touching. In FIGS. 1 and 2, the shape of SSI device 100 may be deliberately adjusted (e.g., to adjust for different users). For instance, the shape of SSI device 100 may be configured to plastically deform, in response to a force that is stronger than those that occur during a typical use session. Or, for instance, SSI device 100 may include one or more sliders or extensions that are configured to change length or shape.

Muscles

In some implementations, during internal articulation, an SSI device detects neuronal activation of muscles. During internal articulation, efferent nerve impulses are sent from the sensorimotor cortex (brain) through cranial nerves which innervate muscles. The neuronal activation of these muscles may be detected as a myoneural signal. In some implementations, one or more of the following muscles ("Articulator Muscles") are neurologically activated during internal articulation: geniohyoid, mylohyoid, genioglossus, superior longitudinal, inferior longitudinal, transverse, vertical, hyoglossus, palatoglossus, styloglossus, levator palatini, musculus uvulae, tensor palatini, palatopharyngeus, superior pharyngeal constrictor, medial pharyngeal constrictor, and inferior pharyngeal constrictor. In some cases, during internal articulation, little or no movement of the Articulator Muscles occurs. The Articulator Muscles are muscles that would, in ordinary speech, be employed for articulation.

Electrodes

In illustrative implementations, the SSI device houses electrodes that measure voltages at the skin of a user, in order to detect internal articulation by the user. A voltage signal of interest that is measured at an electrode may be produced during internal articulation at neuromuscular junctions in muscles. These muscles may be muscles that would, in ordinary speech, be employed for articulation. These muscles may, in some cases, be at a substantial distance from an electrode, rather than immediately below the region of the skin that the electrode is touching.

In illustrative implementations, the greater the distance that an electrode is from the source of the signal of interest (e.g., a group of muscles in which the signal of interest is being generated), the more the signal of interest is attenuated at the electrode. For instance, in some cases, the voltage of the signal of interest at the electrode is 1/r times the voltage of the signal at its source, where r is the distance between the electrode and the source.

Figure 3:
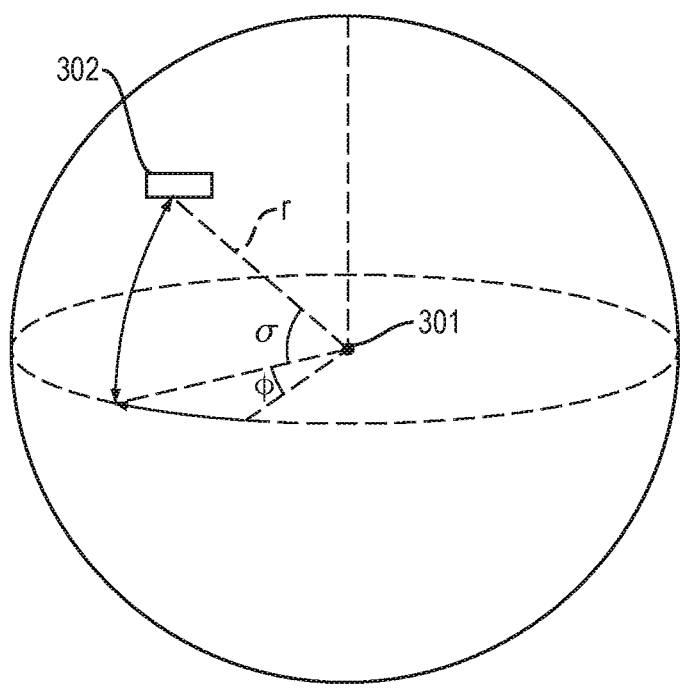
FIG. 3 is a conceptual diagram that shows attenuation of voltage.

FIG. 3 is a conceptual diagram that shows attenuation of voltage. In the example shown in FIG. 3, a signal of interest that is characteristic of internal articulation is generated at source 301. For instance, source 301 may be the centroid of a set of neuromuscular junctions in a group of muscles that are neuronally activated during internal articulation. Electrode 302 is attached to the user's skin, at a distance r from source 301. In FIG. 3, the greater the distance r (between electrode 302 and source 301), the lower the voltage of the signal of interest at electrode 302, all other things being equal. For instance, in some cases, the voltage of the signal of interest at electrode 302 is 1/r times the voltage of the signal at source 301. In FIG. 3, the electric field may extend from an activated motor unit through subcutaneous layers and through the skin, where voltage is measured by a surface electrode.

In illustrative implementations of this invention, electrodes may be placed in any combination of positions on the user's body. For instance, one or more electrodes may be positioned on the user's head and neck.

Figure 4:
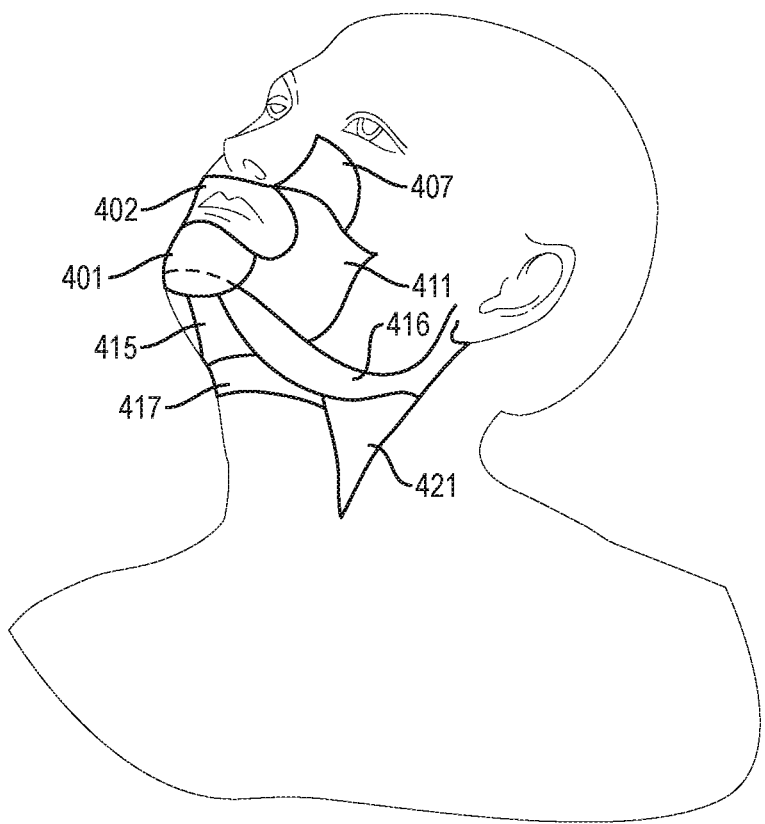
FIG. 4 shows electrode placement regions.

In some implementations of this invention, electrodes are positioned in one or more of the regions shown in FIG. 4. For instance, in some cases, electrodes are positioned at one or more of the following regions of the user's skin: (a) mental (chin) region 401; (b) oral (upper and lower lips) region 402; (c) infraorbital region 407; (d) buccal (maxillary) region 411; (e) submental region 415; (f) submaxillary region 416; (g) hyoid region 417; and (h) carotid fossa region 421. The examples in this paragraph are not limiting; other electrode positions may be employed instead.

Figure 5:
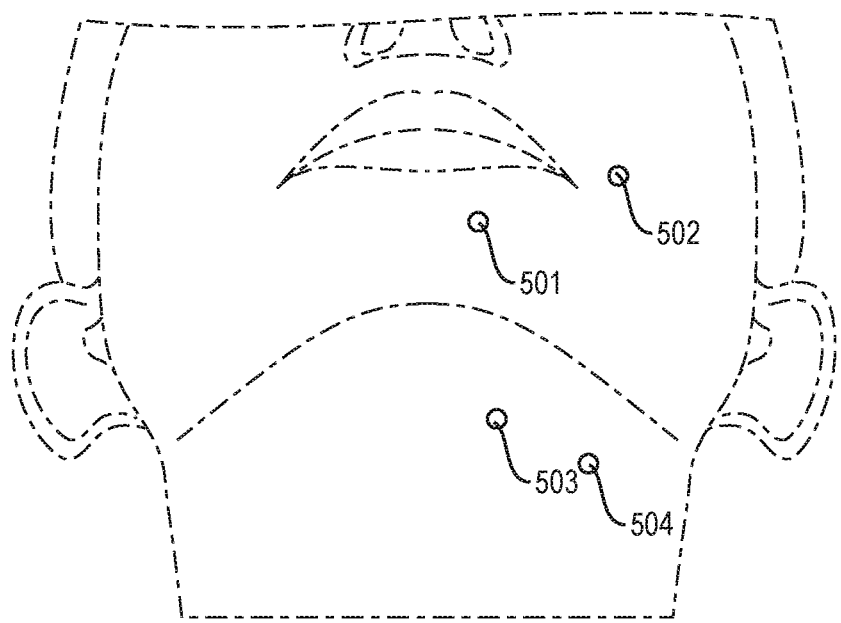
FIGS. 5, 6, 7 and 8 each show a different configuration of electrode positions.

Here are eight examples of electrode positions that may be employed to measure internal articulation:

In a first electrode configuration, electrodes are positioned on the user's skin in the mental (chin), oral (lips) and submaxillary regions (e.g., as shown in FIG. 5).

In a second electrode configuration, electrodes are positioned on the user's skin in the mental (chin), oral (lips), and buccal (maxillary) regions.

In a third electrode configuration, electrodes are positioned on the user's skin in the mental (chin), oral (lips), buccal (maxillary), infraorbital, and submental regions.

Figure 6:
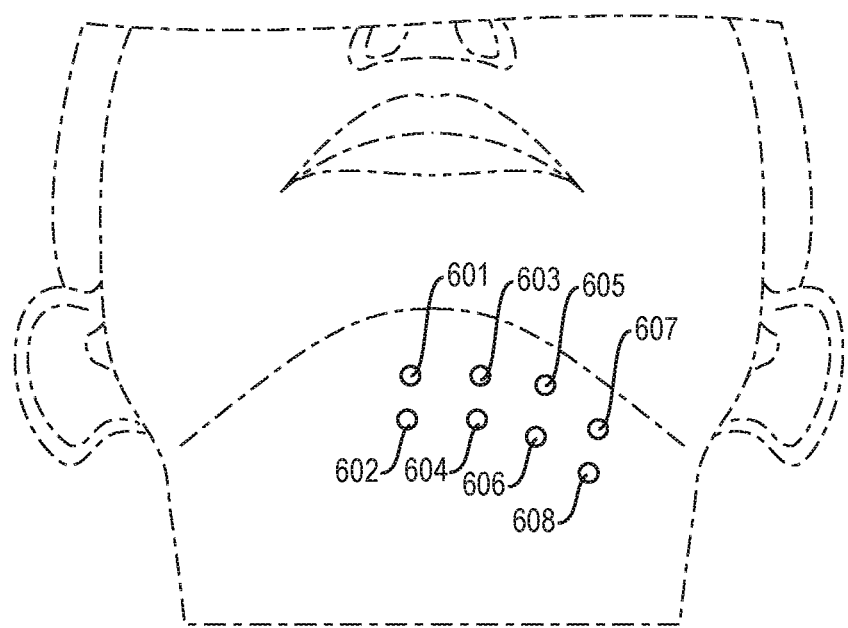

In a fourth electrode configuration, electrodes are positioned on the user's skin in a grid across the submental and submaxillary regions (e.g., as shown in FIG. 6).

In a fifth electrode configuration, electrodes are positioned on the user's skin in a grid across the submaxillary and carotid fossa regions.

Figure 7:
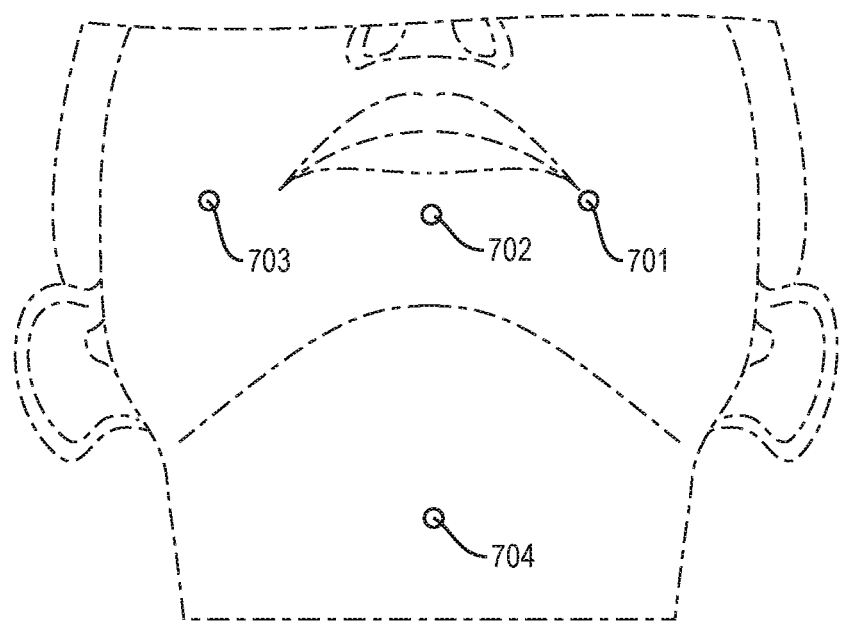

In a sixth electrode configuration, electrodes are positioned on the user's skin in the mental (chin), oral (lips), buccal (maxillary) and hyoid regions (e.g., as shown in FIG. 7).

In a seventh electrode configuration, electrodes are positioned on the user's skin in the hyoid, submental and submaxillary regions.

Figure 8:
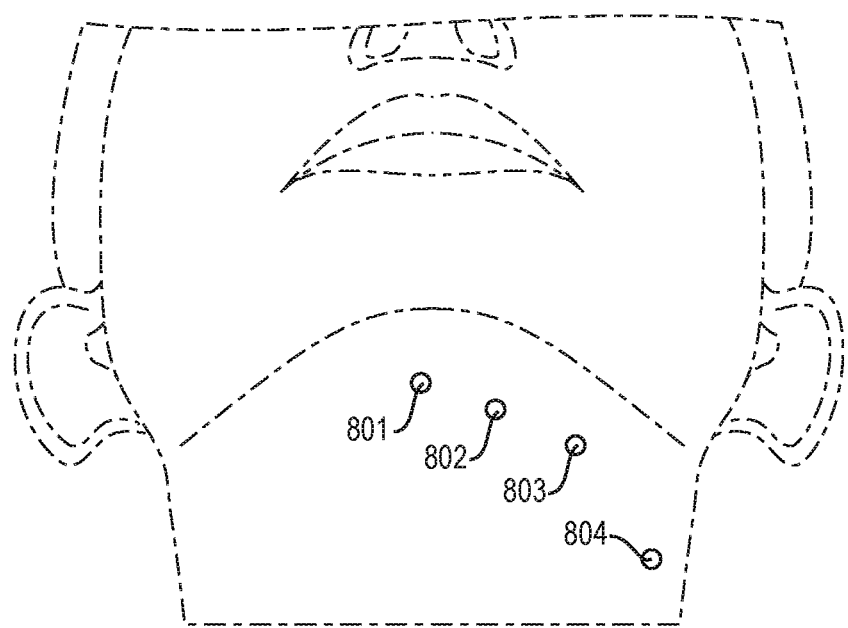

In an eighth electrode configuration, electrodes are positioned on the user's skin in the submental, submaxillary and carotid fossa regions (e.g., as shown in FIG. 8).

The preceding eight examples are non-limiting; other combinations of electrode positions may be employed.

FIGS. 5, 6, 7 and 8 each show a different configuration of electrode positions.

In FIG. 5, electrode 501 is placed in the mental region. Electrode 502 is placed in the oral region close to the mouth. Electrodes 503 and 504 are positioned in a line in the submaxillary region close to the mandible edge, at a distance 0.5-1 cm inside the jawline.

In FIG. 6, an evenly spaced electrode grid is spread across the submental and submaxillary region. Electrodes 601, 603, 605 and 607 are positioned in a first line across the anterior belly of the digastric, closer to the mandible. Electrodes 602, 604, 606 and 608 are positioned in a second line 0.5 cm below the first line and are spread across the submental and submaxillary regions.

In FIG. 7, electrode 702 is placed at the center of the mental region. Electrode 701 is placed in the oral region in close proximity to the mouth. Electrode 703 is placed on the opposite side of the craniocaudal axis, in the buccal region. Electrode 704 is the placed in the center of the hyoid region.

In FIG. 8, electrode 801 is placed in the submental region 0.4-0.6 cm away from the mandible edge. Electrodes 802 and 803 are placed in the submaxillary region close to the mandible edge. Electrode 804 is placed in the carotid fossa region, along the superior muscle of the omohyoid muscle.

The electrode configurations shown in FIGS. 5, 6, 7 and 8 are non-limiting examples; other electrode configurations may be used.

In illustrative implementations, any type of electrode may be employed. For instance, in some cases, any of the following types of electrode may be employed to measure voltage at the skin surface: dry electrodes, wet electrodes, TPE (thermoplastic elastomer) electrodes, silver electrodes, or gold-plated silver electrodes. For example, in some cases, the electrodes comprise gold-plated silver electrodes (e.g., each with a 1.45 mm diameter conductive area), in combination with a conductive paste (e.g., Ten20® polyoxyethylene (20) cetyl ether conductive paste) for reduced contact impedance. Likewise, in some cases, the electrodes comprise passive dry Ag/AgCl electrodes (e.g., each with a 4 mm diameter conductive area).

Each of the electrode configurations described above or shown in FIG. 5, 6, 7 or 8 may measure voltage from all muscles that are activated during internal articulation. This is because the signal of interest may travel away from the source and reach all electrodes, albeit at different intensities. Thus, the positions of the electrodes may be adjusted.

In illustrative implementations, voltage at a given electrode may be measured as a difference between voltage at the given electrode and voltage at a reference electrode.

In each of the electrode configurations described above in this "Electrode" section, a low voltage signal (produced during internal articulation by a user) may have a root mean square (RMS) voltage that is less than one third of the RMS voltage that occurs during ordinary speech of the user.

In each of the electrode configurations described above in this "Electrode" section, a low voltage signal (produced during internal articulation) that is measured at the measurement electrodes may have an RMS voltage that is greater than or equal to 8 microvolts and less than or equal to 20 microvolts. For instance, this may occur if the reference electrode is positioned on the rear side of an earlobe.

In each of the electrode configurations described above in this "Electrode" section, there is also at least one reference electrode and a ground electrode. In some cases: (a) the reference electrode is positioned at the back of an earlobe; and (b) the ground electrode is positioned at the back of the other earlobe. In some other cases: (a) a first reference electrode is positioned at the back of an earlobe; (b) a second reference electrode is positioned at the back of the other earlobe; (c) a ground electrode is positioned at the wrist; and (d) for a given electrode that is employed for measurement, (i) a first voltage is measured relative to the first reference electrode, (ii) a second voltage is measured relative to the second reference electrode, (iii) the first and second voltages are averaged and the resulting average voltage is considered the measured voltage.

Hardware

Figure 9:
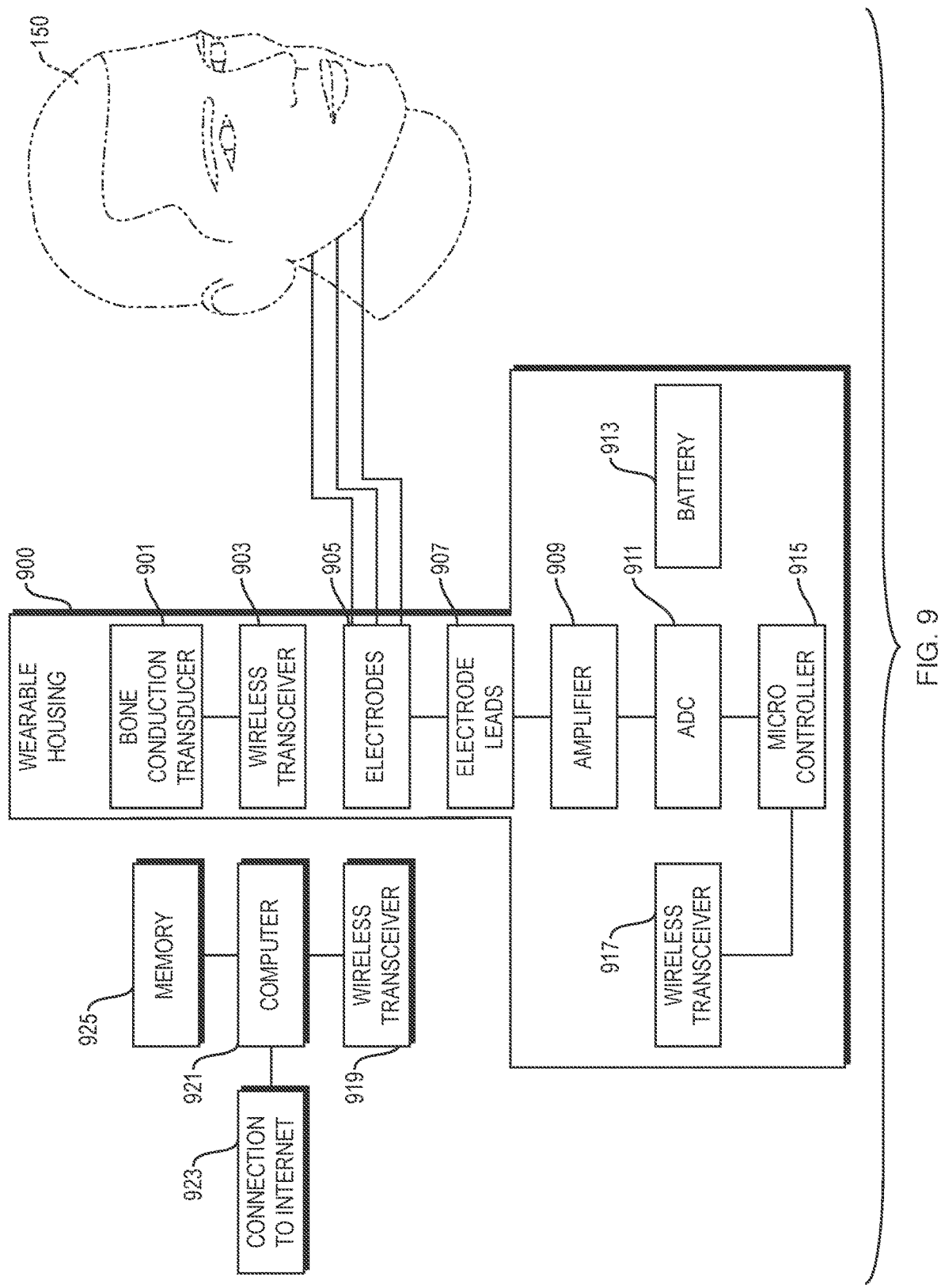
FIG. 9 is a box diagram that shows hardware in a silent speech interface.

FIG. 9 is a box diagram that shows hardware in a silent speech interface. In the example shown in FIG. 9, a wearable housing 900 is configured to be worn on a user's head and neck, and to curve over and partially around (and to be supported by) an ear of the user. Wearable housing 900 includes a bone conduction transducer 901, wireless transceivers 903 and 917, electrodes 905, electrode leads 907, an amplifier 909, an ADC (analog-to-digital converter) 911, a microcontroller 915, and a battery 913. Bone conduction transducer 901 may create vibrations that deliver audio feedback to a user 150. For instance, bone conduction transducer 901 may be positioned (e.g., touching the user's hair or scalp) adjacent to a bony protuberance behind the user's ear. Wireless transceiver 903 may receive wireless signals that encode audio feedback, and may convert these into digital or analog signals, and may send the digital or analog signals to bone conduction transducer 901. Electrodes 905 may measure voltage at positions on the user's skin (e.g., positions on the user's head and neck). Electrode leads 907 may electrically connect electrodes 905 and amplifier 909. Amplifier 909 may amplify analog voltage signals detected by electrodes 905. ADC 911 may convert this amplified analog signal to a digital signal and send the digital signal to microcontroller 915. Microcontroller 915 may process this digital signal and may output the processed signal to wireless transmitter 917. Battery 913 may provide power (e.g., via wired connections) to components housed in housing 100. For instance, battery 913 may provide power to bone conduction transducer 901, wireless transceivers 903 and 917, ADC 911, and microcontroller 915.

In FIG. 9, one or more components of the SSI system may be located outside of wearable housing 100. For instance, computer 921, wireless transceiver 919, memory device 925 and connection to internet 923 may each be separate from, and not housed in, wearable housing 100. Computer 921 may receive, via wireless transceiver 919, data that encodes electrode measurements. Computer 921 may analyze this data, by performing NLP (natural language processing) to detect content of internal articulation by user 150. For example, the NLP may analyze the data (which encodes electrode measurements) to recognize words or sentences that are internally articulated by user 150. Computer 921 may obtain data from one or more remote computer servers via the Internet. To do so, computer 921 may access the Internet via connection to internet 923. Computer 921 may output signals that encode audio feedback for the user, and these signals may be converted into wireless format and transmitted by wireless transceiver 919. Computer 921 may store data in, and retrieve data from, memory device 925.

Wireless transceivers 903, 917, 919 may send and receive wireless radio signals in accordance with one or more wireless standards, such as IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTE (long term evolution)), or other IEEE communication standard.

In some cases, connection to internet 923 comprises one or more routers, modems, computer buses, computer ports, network connections, network interface devices, host adapters, wireless modules, wireless cards, signal processors, cables or wiring.

Method

Figure 10:
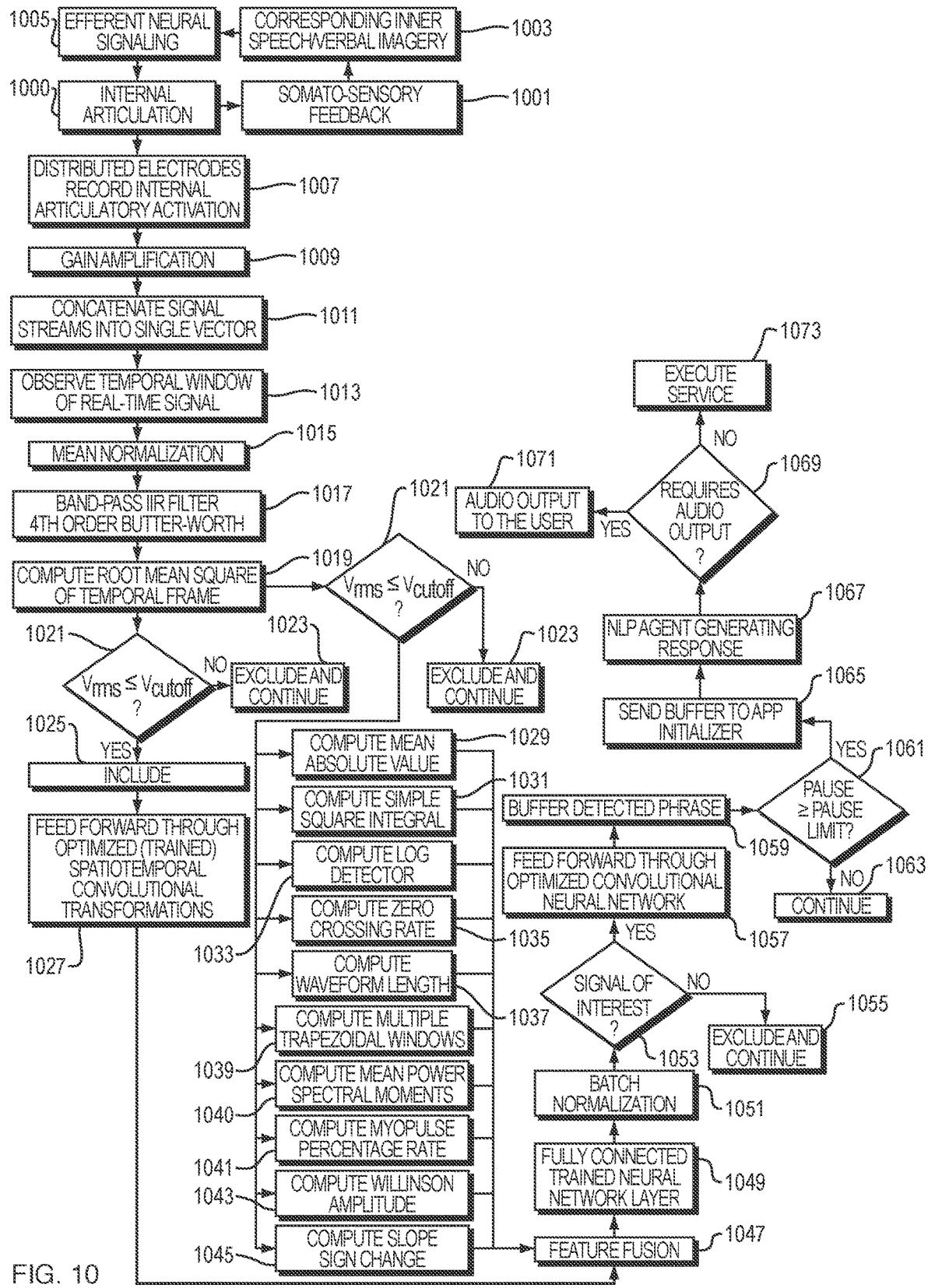
FIG. 10 is a flowchart for a method of detecting internal articulation and responding to it.

FIG. 10 is a flowchart for a method of detecting internal articulation and responding to it.

In FIG. 10: (a) a first CNN may extract relevant windows out of real time noisy data; and (b) a second CNN may classify a signal (which comprises measurements taken during these windows) into words. In FIG. 10, the first CNN performs steps 1027, 1049 and 1051 and may also perform step 1047. In FIG. 10, a second CNN performs step 1057.

In the example shown in FIG. 10, a user's inner speech (e.g., mental speech) or mental verbal imagery 1003 may produce efferent nerve signaling 1005, which in turn may cause internal articulation 1000 (e.g., neural activation at neuromuscular junctions in Articulator Muscles). This internal articulation 1000 may produce somato-sensory feedback 1001 to the user.

In FIG. 10, distributed electrodes may record neural activations that occur during internal articulation 1007. One or more amplifiers may amplify 1009 the recorded signals (e.g., with a 24× gain). The amplified signals from multiple electrodes may be concatenated into a signal vector 1011 for each temporal window of a real-time signal 1013. For instance, each temporal window may be four seconds. For example, in some cases, there are three electrodes and a 4 second time window, and a single 1D vector comprises (in the following order) data encoding measurements from the first electrode during that window, then data encoding measurements from the second electrode during that window, and then measurements from the third electrode during that window.

In FIG. 10, the 1D vector of measurements may be mean normalized 1015 (e.g., by dividing each measurement in the vector by the mean of the measurements in the vector). The normalized vector may be bandpass filtered 1017, such as by a digital 4th-order Butterworth filter. For instance, the passband of the filter may be from 1 Hz to 10 Hz, or from 1.3 Hz to 50 Hz. In addition, the vector may optionally be notch filtered (e.g., with a narrow bandstop centered at 60 Hz) to remove artifacts.

In FIG. 10, the RMS (root mean square) voltage of the temporal frame may be computed 1019 and compared to a cut-off voltage 1021. If the RMS voltage for the temporal window is greater than the cut-off voltage, then the temporal window may be discarded or excluded from further processing 1023.

In FIG. 10, if the RMS voltage for the temporal window is less than or equal to the cut-off voltage, then the mean-normalized, filtered vector for the temporal window may be inputted into a first, 1D convolutional neural network (CNN) which has already been optimized (trained). For instance, the 1D vector of electrode measurements may be fed forward through a first CNN that: (a) performs optimized (trained) spatio-temporal convolutional transformations 1027; (b) performs feature fusion 1047; (c) includes a fully-connected, trained neural network) layer 1049; and (d) performs batch normalization 1051.

In FIG. 10, a computer may calculate one or more features of the 1D vector of voltage measurements. For instance, a computer may calculate the following features: (a) mean absolute value 1029; (b) simple square integral 1031; (c) log detector 1033; (d) zero crossing rate 1035; (e) waveform length 1037; (f) multiple trapezoidal windows 1039; (g) mean power spectral moments 1040; (h) myopulse percentage rate 1041; (i) Willison amplitude 1043; and (j) slope sign change 1045.

In FIG. 10, mean absolute value (MAV) 1029 for a time window may be calculated as $$MAV = \frac{1}{N}\sum_{i=1}^{N} |x_i|,$$

where N is the number of measurements in the time window and $x_i$ is the voltage of the $i^{th}$ measurement.

In FIG. 10, simple square integral (SSI) 1031 for a time window may be calculated as $SSI = \sum_{i=1}^{N} x_i^2$, where N is the number of measurements in the time window and $x_i$ is the voltage of the $i^{th}$ measurement.

In FIG. 10, log detector (LOG) 1033 for a time window may be calculated as $$LOG = e^{\frac{1}{N}\sum_{i=1}^{N} \log(|x_i|)},$$

where N is the number of measurements in the time window, $x_i$ is the voltage of the $i^{th}$ measurement, and e is Euler's number.

In FIG. 10, zero crossing rate 1035 for a time window may be calculated as the number of times that the voltage values of the measurements cross zero during the time window. Alternatively, zero crossings may be counted only if they exceed (in magnitude) a threshold. The threshold may tend to filter out low-voltage fluctuations or background noise. For instance, zero crossing rate (ZC) may be calculated as $ZC=\Sigma_{i=1}^{N-1}[sgn(x_i \times x_{i+1}) \cap |x_i - x_{i+1}| \geq threshold]$, where N is the number of measurements in the time window, $x_i$ is the voltage of the $i^{th}$ measurement, and $sgn(x_i)$ is equal to 1 if $x_i$ is greater than or equal to the threshold and is zero otherwise.

In FIG. 10, waveform length (WL) 1037 for a time window may be calculated as $WL=\Sigma_{i=1}^{N-1}|x_{i+1}-x_i|$, where N is the number of measurements in the time window and $x_i$ is the voltage of the $i^{th}$ measurement.

In FIG. 10, multiple trapezoidal windows (MTW) 1039 for a time period may be calculated as $MTW_k=\Sigma_{i=0}^{N-1}(x_i^2 w_{i-i_k})$, k=1, . . . , K, where N is the number of measurements in the time period, $x_i$ is the voltage of the $i^{th}$ measurement in the time period, w is trapezoidal window, and K is the number of trapezoidal windows.

In FIG. 10, mean power spectral moments 1040 may be calculated as follows: The first spectral moment (SM1) is $SM1=\Sigma_{j=1}^{M}P_j f_j$; the second spectral moment (SM2) is $SM2=\Sigma_{j=1}^{M}P_j f_j^2$; the third spectral moment (SM3) is $SM3=\Sigma M_{j=1}^{M}P_j f_j^3$; and so on, where $f_j$ is frequency of the spectrum at frequency bin j, $P_j$ is the power spectrum at frequency bin j, and M is length of the frequency bin (e.g., number of frequency bins).

In FIG. 10, myopulse percentage rate (MYOP) 1041 may be an average value of myopulse output which is defined as one when absolute value of the vector exceeds a threshold value. In some cases, myopulse percentage rate (MYOP) is calculated as $MYOP=\Sigma_{i=1}^{N}[f(x_i)]$, where N is the number of measurements in the time window, $x_i$ is the voltage of the $i^{th}$ measurement, and $f(x_i)$ is equal to 1 if $x_i$ is greater than or equal to a threshold and is zero otherwise.

In FIG. 10, Willison amplitude (WAMP) 1043 for a time window may be calculated $WAMP=\Sigma_{i=1}^{N-1}[f(|x_i-x_{i+1}|)]$, where N is the number of measurements in the time window, $x_i$ is the voltage of the $i^{th}$ measurement, and f(x) is equal to 1 if x is greater than or equal to a threshold and is zero otherwise.

In FIG. 10, slope sign change (SSC) 1045 may be calculated as the number of times that the slope of the signal changes sign during the time window. Alternatively, in some cases, changes in slope sign are counted only if they exceed (in magnitude) a threshold. The threshold may tend to filter out background noise. For instance, SSC may be calculated as $SSC=\Sigma_{i=2}^{N-1}[f[(x_i-x_{i-1}) \times (x_i-x_{i+1})]]$, where N is the number of measurements in the time window, $x_i$ is the voltage of the $i^{th}$ measurement, and f(x) is equal to 1 if x is greater than or equal to a threshold and is zero otherwise.

In FIG. 10, feature fusion 1047 may be performed. For instance, the feature fusion 1047 may be performed with features 1029, 1031, 1033, 1035, 1037, 1039, 1040, 1041, 1043, 1045.

In FIG. 10, in some cases, the first CNN (which performs steps 1027, 1047, 1049 and 1051) extracts a signal of interest from noisy data.

Among other things, the first CNN may effectively impose a floor for internal articulation rate (e.g., a floor for the number of phonemes internally articulated by a user per unit of time). Thus, the first CNN may effectively impose a floor that eliminates "dead time" which occurs when the user is not internally articulating. The CNN may effectively delete (not pass on) signal portions (e.g., time windows) where the internal articulation rate is below the floor. Likewise, the first CNN may effectively determine that other parts of a signal (even above the floor) are not of interest and thus may delete (not allow to pass) those other parts of the signal that are not of interest.

In FIG. 10, the first CNN may determine whether a signal (e.g. a vector of measurements for a time window) is a signal of interest 1053. If the signal is not a signal of interest, then it may be disregarded 1055. If the signal (e.g. a vector of measurements for a time window) is a signal of interest, then the signal may be fed forward through a second CNN which has already been optimized (trained) 1057.

In FIG. 10, an internally articulated phrase may be detected in the signal and may be temporarily stored in memory in data buffer 1059. A computer may determine: (a) the time elapsed between each word and the next word; and (b) whether the time elapsed exceeds a pause limit 1061. If the elapsed time is less than the pause limit, then this indicates that the user intended the new word to be part of the same phrase, and this new word is also added to the data buffer and the process continues 1063. If the elapsed time is greater than or equal to the pause limit and there are one or more words in the data buffer, this may indicate that the user has completed a phrase, and thus: (a) the buffered phrase may be inputted into a NLP (natural language processing) algorithm and deleted from the data buffer; and (b) the elapsed time between words may be reset to zero 1065.

Thus, in FIG. 10, the system may count time elapsed during a pause in internal articulation. If a pause between a new word and the most recent word that preceded it is less than a pause limit (e.g., 4 seconds), then the new word is added to a data buffer. If the pause is more than the pause limit (i.e., if the pause is "long"), then buffered words for the phrase since the last long pause is inputted into an NLP (natural language processor). Thus, effectively: (a) the system may buffer data regarding a group of phonemes until a pause exceeds the pause limit (e.g., 4 seconds); and then (b) the system may forward data regarding the group of phonemes to the NLP.

An NLP algorithm: (a) may detect the content of an internally articulated phrase or phrases; and (b) determine a response 1067. A computer may determine whether the response involves an audio output 1069. If the response involves audio output, a transducer (e.g., earphone or bone conduction transducer) may provide audio output to a user 1071. This audio output may be audible to the user wearing the SSI device but may be inaudible to persons near the user. If the response does not involve audio output, the SSI device may perform another service (such as sending a message, or controlling a luminaire or other appliance) 1073.

In FIG. 10, a first CNN may perform feature fusion and may detect a signal of interest (e.g., a signal indicative of internal articulation activation). This first CNN may perform steps 1027, 1047, 1049 and 1051 in FIG. 10. This first CNN may include SPTC (spatiotemporal convolution) layers, with ReLU (rectified linear unit) activation function and BN (batch normalization). For instance, this first CNN may comprise the following layers (in the following order): (a) input layer; (b) SPTC layer (with ReLU, then BN); (c) max pooling layer; (d) SPTC layer (with ReLU, then BN); (e) max pooling layer; (f) SPTC layer (with ReLU, then BN); (g) max pooling layer; (h) feature fused layer; (i) fully connected layer (with ReLU, then BN); (j) fully connected layer (with ReLU); and (k) an output layer (with binary cross entropy loss function).

In FIG. 10, a second CNN may perform classification. This second CNN may perform step 1057 in FIG. 10. This second CNN may comprise the following layers (in the following order): (a) input layer; (b) convolutional layer (with ReLU and dropout); (c) max pooling layer; (d) convolutional layer (with ReLU and dropout); (e) max pooling layer; (f) convolutional layer (with ReLU and dropout); (g) max pooling layer; (h) fully connected layer (with ReLU); (i) fully connected layer (with ReLU); and (j) output layer (with softmax loss function). The dropout may enable the CNN to better generalize to other data. For instance, the dropout rate employed in the convolutional layers may be 50%.

The method shown in FIG. 10 is a non-limiting example. This invention may be implemented in other ways.

For instance, feature fusion may be omitted in the first CNN. For instance, in some alternative cases, the first CNN may—without performing feature fusion—detect a signal of interest (e.g., a signal indicative of internal articulation activation). This alternative first CNN may perform steps 1027, 1049 and 1051 in FIG. 10 and may omit step 1047 (feature fusion). This alternative first CNN may comprise the following layers (in the following order): (a) input layer; (b) SPTC layer (with ReLU, then BN); (c) max pooling layer; (d) SPTC layer (with ReLU, then BN); (e) max pooling layer; (f) SPTC layer (with ReLU, then BN); (g) max pooling layer; (h) flatten layer; (i) fully connected layer (with ReLU); (j) fully connected layer (with ReLU); (k) fully connected layer (with ReLU); and (l) output layer (with binary cross entropy loss function).

In some alternative cases, a single CNN comprises two modules, where: (a) the first CNN extracts relevant windows out of real time noisy data; and (b) the second module classifies the signal into words.

In some cases, two neural networks in the SSI device may be trained (backpropagated) as one network.

A wide variety of neural network architectures may be employed. Which architecture is best may depend on the number of instances (size of dataset) at hand. For instance, in some cases, more convolutional layers may be added to the neural network to make it more dense.

This invention is not limited to CNNs. For instance, in some cases, the CNNs may be replaced by one or more machine learning algorithms, such as LSTM (long short-term memory), HMM (Hidden Markov Model), combination of LSTM and CNN, deep Boltzmann machine, deep belief networks, or stacked auto-encoders.

In some implementations, the neural network(s) are trained on training data. For instance, the training data may comprise a set of labeled words (or labeled phonemes) that have been internally articulated. The training data may be internally articulated by multiple different persons, in order to train the SSI device to recognize words that are internally articulated by different persons. Alternatively, training may be customized for a particular user and at least a portion of the training data may comprise labeled words (or labeled phonemes) that were internally articulated by the particular user.

Prototype

The following nine paragraphs describe a prototype of this invention. This prototype differs in many respects from the implementation described in FIG. 10.

In this prototype, signals that are indicative of internal articulation are captured using electrodes on the user's skin, in a facial or neck region. An SSI device houses either TPE (thermoplastic elastomer) plastic, gold-plated silver electrodes (1.45 mm diameter conductive area), in combination with Ten20® (polyoxyethylene (20) cetyl ether) conductive paste for reduced contact impedance, or passive dry Ag/AgCl electrodes (4 mm diameter conductive area).

In this prototype, a reference electrode is placed either on the wrist or the earlobe. Bias-based signal cancellation is employed for canceling approximately 60 Hz line interferences and to achieve higher signal-to-noise (SNR) ratio. The signals are sampled at 250 Hz and differentially amplified at 24× gain.

In this prototype, an opto-isolated external trigger acts as a channel stream with high voltage pulses marking starting and ending events of a silent phrase. Subsequently, the signal streams are wirelessly sent to an external computing device for further processing.

In this prototype, the signals go through multiple preprocessing stages. The signals are fourth order butterworth filtered (1.3 Hz to 50 Hz). The high pass filter is used in order to prevent signal aliasing artifacts. The low pass filter is applied to avoid movement artifacts in the signal. A notch filter is applied at 60 Hz to nullify line interference in hardware. The notch filter is applied, despite the butterworth filter, because of the gentle roll-off attenuation of the latter.

In this prototype, signal streams are separated into components through Independent Component Analysis (ICA) to further remove movement artifacts. The signals are digitally rectified, normalized to a range of 0 to 1 and concatenated as integer streams. The streams are sent to a mobile computational device through Bluetooth® LE, which subsequently sends the data to the server hosting the recognition model to classify silent words. This protocol facilitates use of the SSI device as a wearable device.

In this prototype, the signal undergoes a representation transformation before being input to the recognition model. A running window average is employed to identify and omit single spikes (>30 μV above baseline) in the stream, with amplitudes greater than average values for nearest 4 points before and after. Optionally, mel-frequency cepstral coefficient based representations may be employed to characterize the envelopes of human speech. The signal stream is framed into 0.025 s windows, with a 0.01 s step between successive windows, followed by a periodogram estimate computation of the power spectrum for each frame. A Discrete Cosine Transform (DCT) may be applied to the log of the mel filterbank applied to the power spectra. This allows the SSI device to effectively learn directly from the processed signal without explicitly detecting any features.

In this prototype, the feature representation is passed through a 1-dimensional convolutional neural network to classify into word labels with the architecture described as follows. A hidden layer convolves 400 filters of kernel size 3 with stride 1 with the processed input and is then passed through a rectifier nonlinearity. This is subsequently followed by a max pooling layer. This unit is repeated twice before globally max pooling over its input. This is followed by a fully connected layer of dimension 200 passed through a rectifier nonlinearity which is followed by another fully connected layer with a sigmoid activation.

In this prototype, the network is optimized using a first order gradient descent and parameters are updated during training. The network is regularized using a 50% dropout in each hidden layer to enable the network to generalize better on unseen data. The neural network is trained on a single NVIDIA® GeForce® Titan X GPU (graphics processing unit). In this prototype, this network architecture is employed to classify multiple categories of vocabulary datasets.

For this prototype, a training data corpus was collected from 3 participants (1 female, average age of 29.33 years) and was used to train a classifier. The training data corpus has approximately 31 hours of internally articulated words recorded in different sessions to be able to regularize the recognition model for session independence. The training data corpus comprises multiple datasets. For instance, in one category of the data corpus, the word labels are numerical digits (0-9) along with fundamental mathematical operations (times, divide, add, subtract and percent) to facilitate externalizing arithmetic computations through the interface. An external trigger signal is employed to slice the data into word instances. In each recording session, signals were recorded for randomly chosen words from a specific vocabulary set. This data was used to train the recognition model for various applications.

The prototype described in the preceding nine paragraphs is a non-limiting example of this invention. This invention may be implemented in other ways.

User Interface

In some implementations, the SSI device includes a user interface (UI). The UI may include: (a) a natural language processor to detect content of user's internally articulated speech and, in some use cases, to generate instructions for audio feedback; (b) software for generating a response to the user's internally articulated speech (which response may, in some use scenarios, comprise audio feedback to the user); and (c) a transducer (e.g., earphone or bone conduction transducer) configured to produce audio feedback. In some use scenarios, the audio feedback repeats the words that the user internally articulated. In other use scenarios, at least a portion of the audio feedback is different than (and in response to) words which the user internally articulated. For instance, if a user internally articulates a request for the current time, the audio feedback may comprise an answer which states the current time.

In some implementations, the SSI device enables personalized bi-directional human-machine interfacing in a concealed and seamless manner, where the element of interaction is in natural language. This may facilitate a complementary synergy between human users and machines, where certain tasks may be outsourced to a computer. After an internally articulated phrase is recognized, the computer may contextually process the phrase according to the relevant application the user accesses (e.g., an IoT application may assign the internally articulated digit 3 to device number 3 whereas a Mathematics application may consider the same input as the actual number 3). The output, thus computed by the application, may then be converted using Text-to-Speech and aurally transmitted to the user. Bone conduction headphones may be employed as the aural output, so as to not impede the user's ordinary hearing. In some cases, an SSI device that performs aural feedback (e.g., via an earphone or bone conduction transducer) operates as a closed-loop input-output platform.

In some implementations, an SSI device may operate in many different applications (modes), either as a closed-loop system, an open-loop system, or a communication system.

Different applications of an SSI device may be initiated by internally articulating corresponding hotwords. For instance, the hotword "IoT" may initiate control of an IoT wireless device control via the user interface. For example, in some cases: (a) the vocabulary sets are modeled as n-gram sequences, where the recognition of a specific word assigns a probability distribution to subsequent vocabulary sets; (b) the probability $p_i$ may be assigned to a vocabulary set $v_i$ based on previous recognition occurrences $i_x$ to $x_{n-1}$ as $P(v_i|x_{n-1} \ldots x_1)=p_i$. For instance, the probability $p_i=1$ may be assigned to vocabulary sets meant for specific applications, in a Markovian dependency arrangement, where each set is detected by a convolutional neural network. This hierarchy may reduce the number of word possibilities to be detected within an application, thereby increasing the robustness of the current system.

In some cases, the UI: (a) operates as a closed-loop interface; (b) operates as an open-loop interface; or (c) facilitates human-to-human communication.

In closed-loop mode, the SSI device may respond to the user's internally articulated queries through aural feedback (which is audible to the user but not to other persons in the vicinity of the user). This aural feedback helps enable a closed-loop, silent and seamless conversation with a computing device.

In some cases, when operating in closed-loop mode, the SSI device performs math calculations. For instance, in some cases, a user may internally articulate an arithmetic expression and the computer may subsequently provide the computed value (of the arithmetic expression) through aural feedback. For example, a user may internally articulate the expression 2581 times 698 divide 2 add 13, and the SSI device may output the answer 900782 to the user, through bone conduction headphones. The SSI device may be used to issue reminders and schedule tasks at specific times, which are aurally outputted to the user at corresponding times, thereby providing memory augmentation to the user. The SSI device may also enable the user to access time using the interface, by silently communicating world clock and the name of a city, within a trained vocabulary set.

In some cases, when operating in closed-loop mode, the SSI device operates as an adjunct to human cognition in a personalized manner. For instance, in some cases, the SSI device plays games (e.g., chess or Go) through bi-directional silent communication, where the user silently conveys the game state and the AI computes and then aurally outputs the next move to be played. This aural output may be delivered via earphones or bone conduction headphones, so that the output is audible to the user but not to other persons.

In some cases, when operating in open-loop mode, the SSI device may be employed as an input modality to control devices or to initiate or request services. For instance, the SSI device may function as an IoT (internet of things) controller, where: (a) a user silently and internally articulates instructions, without any action that is detectable by persons around the user; and (b) in response to the internally articulated instructions, the SSI device controls home appliances, such as by switching on/off home lighting, or by controlling a television or HVAC systems. Likewise, the SSI device may be employed to respond to phone calls. For instance: (a) a user may internally articulate instructions; and (b) the SSI device may respond to a phone call in accordance with the instructions (e.g., by saying "hello", "how are you", "call you later", "what's up", "yes", or "no").

The interface may be personally trained to recognize phrases meant to access specific services. For example, in some use scenarios, an SSI device: (a) may recognize a user's internally articulated phrase "Uber to home"; and (b) may, in response, book transport from the user's current location to the user's home. The interface may also be used as a silent input to Virtual Reality/Augmented Reality applications.

In some implementations, the SSI device facilitates human-to-human communication. For instance, in a meeting, the device may be used as a back-channel to silently communicate with another person. For example, in some cases, a user may internally articulate common conversational phrases and these phrases may be transmitted to an electronic device that is carried by, worn by, or otherwise associated with, another person.

In some implementations, a user may, in response to events in the user's environment, silently communicate to an SSI device (by internal articulation) keywords of interest which are used for training a machine learning algorithm of the SSI device. In addition, in some cases, peripheral devices may directly interface with the system. For instance, lapel cameras and smart-glasses may directly communicate with the SSI device and provide contextual information to, or obtain contextual information from, the SSI device.

Software

In the Computer Program Listing above, seven computer program files are listed. These seven computer program files comprise software employed in a prototype implementation of this invention. To run these as Python™ software files, the filename extension for each would be changed from ".txt" to ".py" Here is a description of these seven computer program files (after changing the file extension to ".py").

The utils.py script has definitions of various functions that are called in other scripts. These include functions used in detecting activation of internal articulation, and functions used in preparing raw data for activation detection and classification. The utils.py script imports the following modules: _future_; six.moves.urllib.request; urlretrieve; sklearn; keras; os; sys; numpy; random; scipy; matplotlib; collections; pickle; pitertools; copy; Levenshtein; difflib; tensorflow; statsmodels.tsa.ar_model; and python_speech_features.mfcc.

The 1DCNN_fft_keras.py function implements a version of a 1D convolutional neural network.

The 1DCNN_keras_from_arnay.py function: (a) imports a glob library; and (b) implements a version of a 1D convolutional neural network.

The digits_keras_no_shuffle_feature_selection.py script describes functions that are used for phrase classification. The digits_keras_no_shuffle_feature_selection.py script also imports the following modules: atexit; json; timeit; itertools; and datetime.

The vad_fused_keras_no_shuffle.py script describes the functions that are used for detecting instances of internal articulation in real-time.

The model_repo.py script: (a) imports the copy module; and (b) is a repository of models employed in classification and detecting internal articulation detection.

The realtime_processing.py script is run on a client which loads the model, processes signals in real-time, detects signal of interest and outputs a detected phrase. The realtime_processing.py script also imports the following modules: binascii; struct; msvcrt; and requests. In this script, some personal details such as server IP, model path have been replaced with placeholders. To run the code, these placeholders may be replaced with appropriate details (e.g., server IP and model path)

This invention is not limited to the software set forth in these seven computer program files. Other software may be employed. Depending on the particular implementation, the software used in this invention may vary.

Computers

In illustrative implementations of this invention, one or more computers (e.g., servers, network hosts, client computers, integrated circuits, microcontrollers, controllers, field-programmable-gate arrays, personal computers, digital computers, driver circuits, or analog computers) are programmed or specially adapted to perform one or more of the following tasks: (1) to control the operation of, or interface with, hardware components of an SSI device, including any electrode, ADC, earphone, bone conduction transducer, or wireless transceiver; (2) to concatenate measurements; (3) to extract a signal of interest from noisy real time data, including by thresholding, feature fusion and performing detection and classification with one or more neural networks (e.g., CNNs); (4) to perform natural language processing; (5) to detect content of internally articulated speech, based on electrode measurements; (6) to calculate a response to internally articulated input; (7) to output instructions to control audio feedback to a user; (8) to output instructions to control another device, such as a luminaire, television or home appliance; (9) to detect content of internally articulated input and, in response to the input, to send a message to another device (e.g., to send a message to another person by sending the message to a device associated with the other person); (10) to receive data from, control, or interface with one or more sensors; (11) to perform any other calculation, computation, program, algorithm, or computer function described or implied herein; (12) to receive signals indicative of human input; (13) to output signals for controlling transducers for outputting information in human perceivable format; (14) to process data, to perform computations, and to execute any algorithm or software; and (15) to control the read or write of data to and from memory devices (tasks 1-15 of this sentence referred to herein as the "Computer Tasks"). The one or more computers (e.g. 915, 921) may, in some cases, communicate with each other or with other devices: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied herein. For example, in some cases, instructions encoded in a tangible, non-transitory, computer-accessible medium comprise instructions for a computer to perform the Computer Tasks.

Network Communication

In illustrative implementations of this invention, electronic devices (e.g., 901, 915, 921) are configured for wireless or wired communication with other devices in a network.

For example, in some cases, one or more of these electronic devices each include a wireless module for wireless communication with other devices in a network. Each wireless module (e.g., 903, 917, 919) may include (a) one or more antennas, (b) one or more wireless transceivers, transmitters or receivers, and (c) signal processing circuitry. Each wireless module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables or wiring.

In some cases, one or more computers (e.g., 915, 921) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTE (long term evolution)), or other IEEE communication standard.

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

Unless the context clearly indicates otherwise, "audible" means audible by unaided human hearing.

"Articulator Muscles" is defined above.

To compute "based on" specified data means to perform a computation that takes the specified data as an input.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

A non-limiting example of "detecting" internal articulation is detecting neural activation of muscles that is caused by, triggered by, or involved in the internal articulation.

For an event to occur "during" a time period, it is not necessary that the event occur throughout the entire time period. For example, an event that occurs during only a portion of a given time period occurs "during" the given time period.

The term "e.g." means for example.

"Euler's number" means the unique number whose natural logarithm is equal to one. Euler's number is a constant that is approximately equal to 2.71828.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Internally articulated speech" means speech by a person that: (a) occurs without any audible sound of speech and without any visible movement of any muscle of the person's face or neck; and (b) occurs at least partially when the person is not exhaling.

A straight line is a non-limiting example of a "line". A curved line is a non-limiting example of a "line".

To say that a first set of electrical signals measured at positions on the user's skin during a given temporal window is "low-voltage" means that the first set of signals (taken together) have a root mean square (RMS) voltage during the given temporal window that is less than one half of the RMS voltage of electrical signals that would be measured at the same positions on the user's skin during a second temporal window of equal length as the given temporal window, while the user engaged in mouthed, ordinary speech. A set of electrical signals during internally articulated speech may be "low voltage" even if measurements are not actually taken during ordinary speech. In other words, the first sentence of this definition specifies—by comparison to what would occur in ordinary speech—an RMS voltage level below which a signal is "low-voltage".

To say that X "occurs at least partially when" Y occurs means that X occurs at a set of times, which set includes times when Y occurs and may include other times.

To say that electrodes are positioned "on the skin" means that the electrodes are touching: (a) the skin; or (b) a conductive material that is touching the skin.

The term "or" is inclusive, not exclusive. For example, A or B is true if A is true, or B is true, or both A and B are true.

Also, for example, a calculation of A or B means a calculation of A, or a calculation of B, or a calculation of A and B.

"Ordinary speech" means speech that: (a) occurs while exhaling and while vocal cords are vibrating; and (b) is audible.

A parenthesis is simply to make text easier to read, by indicating a grouping of words. A parenthesis does not mean that the parenthetical material is optional or may be ignored.

As used herein, the term "set" does not include a group with no elements.

Unless the context clearly indicates otherwise, "some" means one or more.

Non-limiting examples of "speech", as that term is used herein, include: (a) ordinary speech; (b) verbal ideation, including reading silently or thinking verbally; (c) mental intent to speak; (d) silently forming words in the vocal tract; and (e) silently and mentally forming words while being aware of speech muscles.

As used herein, "speech muscles" means muscles that are, during ordinary speech, employed in phonation or articulation.

As used herein, "speech articulator muscles" means muscles that are, during ordinary speech, employed in articulation.

As used herein, a "subset" of a set consists of less than all of the elements of the set.

The term "such as" means for example.

To say that a machine-readable medium is "transitory" means that the medium is a transitory signal, such as an electromagnetic wave.

Unless the context clearly indicates otherwise, "visible" means visible to unaided human sight.

To say that X occurs "without any visible movement of any muscle of the person's face or neck" means that no muscle of the person's face or neck visibly moves while X is occurring.

A number is a non-limiting example of a "word".

Except to the extent that the context clearly requires otherwise, if steps in a method are described herein, then the method includes variations in which: (1) steps in the method occur in any order or sequence, including any order or sequence different than that described herein; (2) any step or steps in the method occur more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; (7) one or more steps occur simultaneously, or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. Unless the context clearly indicates otherwise, any definition or clarification herein of a term or phrase applies to any grammatical variation of the term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) taking measurements of a set of electrical signals at positions on a user's skin, which skin is part of the user's head or neck; and (b) analyzing the measurements to recognize content of internally articulated speech by the user; wherein at least a portion of the internally articulated speech occurs when the user is not exhaling. In some cases, analyzing the measurements includes identifying temporal windows during which the electrical signals are low-voltage. In some cases, analyzing the measurements includes identifying temporal windows during which each electrical signal, in the set of electrical signals, occurs at a specific position on the user's skin and has a root mean square (RMS) voltage, which RMS voltage: (a) is greater than or equal to 8 microvolts and less than or equal to 20 microvolts; and (b) is the RMS potential difference between voltage at the specific position and voltage at a reference electrode that is positioned on skin of an ear of the user. In some cases, the content which is recognized comprises one or more words. In some cases, the method further comprises providing audio feedback to the user, via sound vibrations produced by an earphone or bone conduction transducer. In some cases, the audio feedback comprises words that are at least part of the content of the internally articulated speech. In some cases, the audio feedback comprises words that are not part of the content of the internally articulated speech. In some cases, the audio feedback provides information requested by the internally articulated speech. In some cases: (a) the audio feedback provides information requested by the internally articulated speech; and (b) the method further comprises obtaining the information from a computer server via the Internet. In some cases, the method further comprises controlling at least one device in accordance with instructions, which instructions were at least part of the content of the internally articulated speech. In some cases, the method further comprises sending a message that includes at least a portion of the content of the internally articulated speech. In some cases, the method further comprises: (a) sending, to a device associated with a person other than the user, a first message that includes at least a portion of the content of the internally articulated speech; (b) receiving a second message from the device; (c) recognizing content of the second message; and (d) providing audio feedback to the user, which audio feedback comprises words that are part of the content of the second message. In some cases, the measurements comprise measurements of electrical voltage with electrodes. In some cases: (a) the electrodes comprise one or more reference electrodes and one or more other electrodes; and (b) the other electrodes are positioned on skin of the user in one or more of the following skin regions: (i) mental; (ii) oral; (iii) infraorbital; (iv) buccal; (v) submental; (vi) submaxillary; (vii) hyoid; and (viii) carotid fossa. In some cases, the one or more reference electrodes are positioned on regions of skin of the user, which regions are part of one or more ears of the user or of one or more arms of the user. In some cases, the analyzing the measurements includes inputting data into one or more neural networks, where the data encodes the measurements. Each of the cases described above in this paragraph is an example of the method described in the first sentence of this paragraph, and is also an example of an embodiment of this invention that may be combined with other embodiments of this invention.

In some implementations, this invention is an apparatus comprising: (a) one or more electrodes; and (b) one or more computers; wherein (i) the electrodes are configured to take measurements of a set of electrical signals at positions on a user's skin, and (ii) the one or more computers are programmed to analyze the measurements to recognize content of internally articulated speech by the user. In some cases, the one or more computers are programmed to identify temporal windows during which the electrical signals are low-voltage. In some cases, the one or more computers are programmed to identify temporal windows during which each electrical signal, in the set of electrical signals, occurs at a specific position on the user's skin and has a root mean square (RMS) voltage, which RMS voltage: (a) is greater than or equal to 8 microvolts and less than or equal to 20 microvolts; and (b) is the RMS potential difference between voltage at the specific position and voltage at a reference electrode that is positioned on skin of an ear of the user. In some cases: (a) the apparatus further comprises a transducer, which transducer comprises an earphone or bone conduction transducer; and (b) the transducer is configured to provide audio feedback to the user. Each of the cases described above in this paragraph is an example of the apparatus described in the first sentence of this paragraph, and is also an example of an embodiment of this invention that may be combined with other embodiments of this invention.

Each description herein (or in the Provisional) of any method, apparatus or system of this invention describes a non-limiting example of this invention. This invention is not limited to those examples, and may be implemented in other ways.

Each description herein (or in the Provisional) of any prototype of this invention describes a non-limiting example of this invention. This invention is not limited to those examples, and may be implemented in other ways.

Each description herein (or in the Provisional) of any implementation, embodiment or case of this invention (or any use scenario for this invention) describes a non-limiting example of this invention. This invention is not limited to those examples, and may be implemented in other ways.

Each Figure herein (or in the Provisional) that illustrates any feature of this invention shows a non-limiting example of this invention. This invention is not limited to those examples, and may be implemented in other ways.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are also within the scope of the present invention. Numerous modifications may be made by those skilled in the art without departing from the scope of the invention. Also, this invention includes without limitation each combination and permutation of one or more of the items (including hardware, hardware components, methods, processes, steps, software, algorithms, features, or technology) that are described herein.

What is claimed:

1. A method comprising:
   (a) taking measurements of a set of electrical signals at positions on a user's skin, which skin is part of the user's head or neck, and which electrical signals are generated by neural activation of speech articulator muscles; and
   (b) analyzing the measurements to recognize content of internally articulated speech by the user;
   wherein at least a portion of the internally articulated speech occurs when the user is not exhaling.

2. The method of claim 1, wherein the analyzing the measurements includes identifying temporal windows during which the electrical signals are low-voltage.

3. The method of claim 1, wherein the analyzing the measurements includes identifying temporal windows during which each electrical signal, in the set of electrical signals, occurs at a specific position on the user's skin and has a root mean square (RMS) voltage, which RMS voltage: (a) is greater than or equal to 8 microvolts and less than or equal to 20 microvolts; and (b) is the RMS potential difference between voltage at the specific position and voltage at a reference electrode that is positioned on skin of an ear of the user.

4. The method of claim 1, wherein the content which is recognized comprises one or more words.

5. The method of claim 1, wherein the method further comprises providing audio feedback to the user, via sound vibrations produced by an earphone or bone conduction transducer.

6. The method of claim 5, wherein the audio feedback comprises words that are at least part of the content of the internally articulated speech.

7. The method of claim 5, wherein the audio feedback comprises words that are not part of the content of the internally articulated speech.

8. The method of claim 5, wherein the audio feedback provides information requested by the internally articulated speech.

9. The method of claim 5, wherein:
   (a) the audio feedback provides information requested by the internally articulated speech; and
   (b) the method further comprises obtaining the information from a computer server via the Internet.

10. The method of claim 1, wherein the method further comprises controlling at least one device in accordance with instructions, which instructions were at least part of the content of the internally articulated speech.

11. The method of claim 1, wherein the method further comprises sending a message that includes at least a portion of the content of the internally articulated speech.

12. The method of claim 1, wherein the method further comprises:
   (a) sending, to a device associated with a person other than the user, a first message that includes at least a portion of the content of the internally articulated speech;
   (b) receiving a second message from the device;
   (c) recognizing content of the second message; and
   (d) providing audio feedback to the user, which audio feedback comprises words that are part of the content of the second message.

13. The method of claim 1, wherein the measurements comprise measurements of electrical voltage with electrodes.

14. The method of claim 13, wherein:
(a) the electrodes comprise one or more reference electrodes and one or more other electrodes; and
(b) the other electrodes are positioned on skin of the user in one or more of the following skin regions: (i) mental; (ii) oral; (iii) infraorbital; (iv) buccal; (v) submental; (vi) submaxillary;
(vii) hyoid; and (viii) carotid fossa.

15. The method of claim 14, wherein the one or more reference electrodes are positioned on regions of skin of the user, which regions are part of one or more ears of the user or of one or more arms of the user.

16. The method of claim 1, wherein the analyzing the measurements includes inputting data into one or more neural networks, where the data encodes the measurements.

17. Apparatus comprising:
(a) electrodes; and
(b) one or more computers;
wherein
(i) the electrodes are configured to take, at positions on a user's skin, measurements of a set of electrical signals that are generated by neural activation of speech articulator muscles, and
(ii) the one or more computers are programmed to analyze the measurements to recognize content of internally articulated speech by the user.

18. The apparatus of claim 17, wherein the one or more computers are programmed to identify temporal windows during which the electrical signals are low-voltage.

19. The apparatus of claim 17, wherein the one or more computers are programmed to identify temporal windows during which each electrical signal, in the set of electrical signals, occurs at a specific position on the user's skin and has a root mean square (RMS) voltage, which RMS voltage: (a) is greater than or equal to 8 microvolts and less than or equal to 20 microvolts; and (b) is the RMS potential difference between voltage at the specific position and voltage at a reference electrode that is one of the electrodes and is positioned on skin of an ear of the user.

20. The apparatus of claim 17, wherein:
(a) the apparatus further comprises a transducer, which transducer comprises an earphone or bone conduction transducer; and
(b) the transducer is configured to provide audio feedback to the user.

* * * * *